United States Patent [19]

Ishibe et al.

[11] 4,351,973

[45] Sep. 28, 1982

[54] STABILIZED METHYLCHLOROFORM

[75] Inventors: Nobuyuki Ishibe; Warren F. Richey, both of Lake Jackson, Tex.

[73] Assignee: The Dow Chemical Company, Midland, Mich.

[21] Appl. No.: 194,512

[22] Filed: Oct. 6, 1980

[51] Int. Cl.³ .............................................. C07C 17/42
[52] U.S. Cl. .................................... 570/104; 570/108; 570/109; 570/114; 570/118; 252/394; 252/396; 252/403
[58] Field of Search ............... 570/104, 108, 109, 114, 570/118; 252/403, 394, 396

[56] References Cited

U.S. PATENT DOCUMENTS

| | | | |
|---|---|---|---|
| 2,870,094 | 1/1959 | Cathcart | 570/114 |
| 3,049,571 | 8/1962 | Brown | 570/118 |
| 3,128,315 | 4/1964 | Hardies | 570/118 |
| 3,281,480 | 10/1966 | Hardies | 570/118 |
| 3,798,170 | 3/1974 | Petering et al. | 570/109 |

FOREIGN PATENT DOCUMENTS 756710  1/1971  Belgium .............................. 570/108

*Primary Examiner*—Delbert E. Gantz
*Assistant Examiner*—Joseph A. Boska
*Attorney, Agent, or Firm*—A. C. Ancona

[57] ABSTRACT

A stabilized methylchloroform for use in vapor degreasing which is stable in the presence of metals which contains pyrazine, dimethoxypropane, an acetylenic alcohol and a nitroalkane or a methylfuran. Such combination prevents corrosion of aluminum, iron, copper and zinc and the decomposition of the solvent.

10 Claims, No Drawings

STABILIZED METHYLCHLOROFORM

BACKGROUND OF THE INVENTION

This invention relates to the stabiization of chlorinated solvents. More particularly, the present invention concerns the stabilization of 1,1,1-trichloroethane in the presence of metallic aluminum, copper, brass and zinc.

Chlorinated hydrocarbons such as trichloroethylene and perchloroethylene are commonly used as solvents in chemical processes, dry cleaning, and metal degreasing. Solvents of this type are subject to slow decomposition and oxidation reactions, particularly in the presence of impurities such as water, traces of acid or metal salts. Corrosion of metal surfaces in containers and process equipment and deterioration of solvent quality by formation of acidic and colored byproducts thereby become serious problems. Inhibitors such as acid scavengers and antioxidants are commonly added to these solvents in order to prevent such degradative reactions. Inhibitor concentrations are normally of the order of one percent by weight or less.

1,1,1-trichloroethane poses a particularly difficult stabilization problem because of its unusual reactivity with certain metals, notably aluminum. Traces of metal salts, moisture, or other impurities are not needed to initiate the 1,1,1-trichloroethane-aluminum reaction, for this reaction occurs spontaneously on a freshly exposed aluminum surface with spectacular results, converting the solvent and the metal surface in a few minutes to a blackened mass of acidic, carbonaceous material and aluminum salts. Conventional acid acceptor stabilizers cannot be depended upon to inhibit the aluminum-1,1,1-trichloroethane reaction and suitable inhibitors must be discovered by independent investigation. The search has yielded few effective compounds and these show little or no obvious pattern of structure. Typical 1,1,1-trichloroethane formulations contain about five percent by weight of inhibitor which is usually a combination of compounds to inhibit reaction of the solvent with a variety of metals.

Among numerous compounds mentioned as inhibitors for methylchloroform in the presence of aluminum is pyrazine. U.S. Pat. No. 3,798,170 discloses the use of pyrazine as a stabilizer of methylchloroform against aluminum, both in the anhydrous solvent and when water is present. While pyrazine apparently protects aluminum under such conditions, some indication is given that it is not as effective when other metals, e.g. steel and brass, are present.

SUMMARY OF THE INVENTION

Methylchloroform is stabilized for use in vapor degreasing applications by employing in combination, pyrazine, 2,2-dimethoxypropane, a nitroalkane or as a substitute for the nitroalkane, furan or an alkyl substituted furan which may be in combination with an acetylenic alcohol as stabilizer components. This combination protects against corrosion of aluminum, iron, copper, or brass and zinc.

DETAILED DESCRIPTION OF THE INVENTION

It was found that, although pyrazine in combination with methylchloroform protects the solvent in the presence of aluminum, preventing the decomposition of the solvent and the corrosion of the metal, when the metal copper, or its alloys, e.g. brass, is present that pyrazine alone no longer is effective, but that corrosion of the copper occurs.

In the course of investigating various known stabilizer components, it was discovered 2,2-dimethoxy propane in combination with pyrazine effectively protected the methylchloroform in the presence of both aluminum and copper or brass. Zinc, however, is not protected by these two components in methylchloroform. It was then discovered that by adding (1) a nitroalkane, e.g. nitromethane, nitroethane or a mixture thereof, or (2) furan or an alkylfuran, e.g. methylfuran, in combination with an acetylenic alcohol, e.g. a methylbutynol, methylchloroform can be effectively stabilized in the presence of aluminum, iron, copper, or brass and zinc. The combinations are unique in their ability to protect against these metals since heretofore either dioxane and/or an alkylene oxide was thought to be necessary.

Furan, or an alkylfuran, can be substituted in the above formulation for a part, or all of the nitroalkane.

The ranges of components are: pyrazine 1 to 5% by wt., dimethoxypropane 0.2 to 1.0% by vol., furan or an alkylfuran 0.2 to 4.0% by vol., nitroalkane 2.0 to 4.0% by vol.

When furan or an alkyl-substituted furan is employed in the upper part of the range, e.g. 2 to 4% by volume, then the amount of pyrazine employed may be reduced to 2 to 3% by weight.

The commonly employed 7-day reflux test was conducted on the various combinations mentioned above. The results are shown in Table I.

Seven-Day Reflux Test

Approximately 430 g of methylchloroform solution formulation with pyrazine in combination with other additives (nitroalkanes, methyl furans, etc.) was partitioned by distillation into equal volume fractions. Ten ml aliquots of both fractionated (top and bottom) and unfractionated solutions were refluxed for seven days in the presence of Al-2024, Zn, Cu, brass, steel, or Fe metals, and the stability of the solution was visually rated. The rating given is the number of hours at which metal corrosion and/or discoloration of the solvent was observed. When no corrosion was observed at the end of seven days, it is indicated by >168. Examples of the invention are numbered while comparative (Comp.) examples are lettered.

TABLE I

| Example # | Inhibitor* (%) | Metals | **Rating (hrs.) TF | BF | UF |
|---|---|---|---|---|---|
| Comp. A | PY (3) | Al-2024, | — | — | >168 |
|  |  | Zn | — | — | 69 |
|  |  | Cu, Brass | — | — | 24–48 |
| Comp. B | PY (3) | Al-2024, Zn | >168 | >168 | >168 |
|  | NM (0.4) |  |  |  |  |
|  | NE (0.6) | Steel, Fe |  |  |  |
|  |  | Cu, Brass | 96 | 48 | 120–144 |
| 1 | PY (3) | Al-2024, Zn, | >168 | >168 | >168 |

TABLE I-continued

| Example # | Inhibitor* (%) | Metals | **Rating (hrs.) TF | BF | UF |
|---|---|---|---|---|---|
|  | NM (0.4) NE (0.6) DMP 0.5 | Steel, Fe |  |  |  |
|  | " | Cu, Brass | 144–168 | 144–168 | 144–168 |
| Comp. C | PY (3) DMP (1) | Al-2024, Brass | — | — | >168 |
|  |  | Zn | — | — | 66 |
| 2 | PY (3) DMP (1) MF (0.5) | Al-2024, Zn, Fe, Steel, Cu, Brass | >168 | >168 | >168 |
| Comp. D | PY (3) FN (0.5) MBY (0.5) | Al-2024 | — | — | >168 |
|  |  | Zn, Brass | — | — | 120 |
| 3 | PY (3) MF (0.5) MBY (0.5) DMP (0.75) | Al-2024, Zn Fe, Steel | >168 | >168 | >168 |
|  |  | Brass, Cu | 144 | 144 | 144 |
| 4 | PY (2) NM (0.4) NE (0.6) DMP (0.5) MF (1.5) | Al-2024, Zn Fe, Steel | — | — | >168 |
|  |  | Cu, Brass | — | — | 144–168 |

*PY = pyrazine; NM = nitromethane; NE = nitroethane; DMP = dimethoxypropane; MF = 2-methylfuran; FN = furan; MBY = 2-methyl-3-butyn-2-ol. Pyrazine is expressed as wt. %, while other components are given as vol. %.
**TF = top fraction; BF = bottom fraction; UF = unfractionated.

Two other tests were conducted on the various compositions of the invention and on commercially used degreasing compositions. Descriptions of these tests follow and results of the vapor degreaser simulation and drill cover tests together with the 7-day reflux test are shown in Table II.

Vapor Degreaser Simulation Test

A test to simulate a two chamber vapor degreaser was carried out in a glass apparatus to which a 500 ml round bottom flask (for sump) was connected by a tilted side arm with a 500 ml round bottom flask (for dip) equipped with a condenser. Five hundred ml of a methylchloroform solution formulated with 3 wt. % pyrazine, 0.4 vol. % nitromethane, 0.6 vol. % nitroethane, and 0.5 vol. % 2,2-dimethoxypropane were added to the dip, half of the solution (250 ml) overflowing into the sump. The sump solution was gently boiled, and the dip was kept warm at 68°–70° C. The vapor was condensed into the warm dip flask from which excess solution was returned into the boiling sump solution. After the solution was refluxed for two days, 13.5 ml of mineral oil was added to the sump flask. The solution was refluxed for two days, and then the mixture of the following metals was added to the sump and dip. Metal additions to the sump and dip included 1.5 g of Al-2024 chips, 0.5 g of steel wool, 3.5 g of mossy zinc (only 2.1 g of mossy Zn for the dip), and 3.5 g of 70/30 brass chips. The mixture was refluxed for seven days. No metal corrosion was found.

Drill Cover Test

Test is done under two different conditions: (1) ambient temperature for a formulated solution itself and a mixture of 10% formulated solution with 90% toluene; and (2) nearly boiling temperatures for the formulated solution alone.

Fifty milliliters of a formulated solution is placed in a Pyrex Petri dish. An aluminum coupon is submerged in the solution, and 0.1 mm deep holes are drilled into the surface of the coupon with an electric drill. The coupon is immediately covered with another aluminum coupon of the same type. The Petri dish is then covered, and both the metal surface and solution are rated after 60 minutes. The results are summarized in Table II.

The formulation with pyrazine and nitroalkanes is very effective even in the presence of 90% toluene, which generally promotes attack on aluminum.

The combination pyrazine, dimethoxypropane and nitroalkane, or its equivalent, may be employed without deleterious effect, and sometimes with improved results, when used in conjunction with one or more other known stabilizers. Thus, 1,4-dioxane, i-butyl alcohol, ethylacetate, methylethylketone, dimethylcarbonate have been employed with good results when used with 2% by wt. pyrazine, 1.0% by vol. nitroalkane and 0.5% by vol. 2,2-dimethoxypropane.

TABLE II

| Formulation* | 7-Day Reflux | Vapor Degreaser Simulation | Drill Cover Ambient 0% Toluene | Hot (~65° C.) 0% Toluene | Ambient 90% Toluene |
|---|---|---|---|---|---|
| Ex. 3 (Table I) | P** | P | P | P | F** |
| Ex. 1 (Table I) | P | P | P | P | P |
| Comp. G | P | P | P | P | F |
| Comp. H | P | P | P | P | F |
| Comp. I | P | P | F | F | F |
| Comp. J | P | P | P | P | F |

*Comp. G—3.5% Dioxane (DO) + 0.4% NM + 0.5% Butylene oxide (BO)
Comp. H—1.5% DO + 1.75% MBY + t-amyl alcohol (TAA) + 0.4% NM + 0.6% NE + 0.5% BO
Comp. I—2% MBY + 2% TAA + 0.4% NM + 0.6% NE + 0.75% BO
Comp. J—3% Dioxolane (DOX) + 1.5% MBY + 0.4% NM + 0.6% NE + 0.8% BO
**P = pass the test; F = fail test.

I claim:
1. A stabilized methylchloroform composition comprising a stabilizing amount of (1) pyrazine, (2) 2,2- dimethoxypropane, and (3) a nitroalkane or a furan or an alkylfuran in methylchloroform.

2. The composition of claim 1 wherein the stabilizing components comprise 3% to 10% by weight of the total composition, the remainder being methylchloroform.

3. The composition of claim 2 which additionally contains an acetylenic alcohol.

4. The composition of claim 2 which contains from about 1 to about 5 wt. % pyrazine, from about 0.2 to about 1.0 vol. % 2,2-dimethoxypropane, from about 0.2 to about 4.0% of a nitroalkane or a methylfuran based on total weight of composition.

5. The composition of claim 3 which contains from about 1 to about 3% pyrazine, from about 0.2 to about 1.0% 2,2-dimethoxypropane, from about 0.2 to about 4% of methylfuran and from about 1 to about 2.5% acetylenic alcohol based on total weight of composition.

6. The composition of claim 1, 2, 3 or 4 wherein the nitroalkane is nitromethanes, nitroethane or a mixture thereof.

7. The composition of claim 3 or 5 wherein the acetylenic alcohol is a methylbutynol.

8. The composition of claim 7 wherein the methylbutynol is 3-methyl-2-butyn-3-ol.

9. A method of protecting aluminum, copper, and brass from corrosion in the presence of methylchloroform which comprises adding to said methylchloroform a stabilizing amount of (1) pyrazine, (2) 2,2-dimethoxypropane and (3) a nitroalkane or methylfuran.

10. A method of protecting aluminum, copper, iron and zinc from corrosion in the presence of methylchloroform which comprises adding to said methylchloroform a stabilizing amount of (1) pyrazine, (2) 2,2-dimethoxypropane, (3) a nitroalkane or methylfuran and an acetylenic alcohol.

* * * * *

UNITED STATES PATENT AND TRADEMARK OFFICE
CERTIFICATE OF CORRECTION

PATENT NO. : 4,351,973
DATED : September 28, 1982
INVENTOR(S) : Nobuyuki Ishibe and Warren F. Richey It is certified that error appears in the above—identified patent and that said Letters Patent is hereby corrected as shown below:

Col. 1, line 6; "stabiization" should read --stabilization--.

Col. 2, line 33; "nitroalkane 2.0" should read --nitroalkane 0.2--.

Col. 4, line 40; "sometims" should read --sometimes--.

Col. 4, line 61; "t-amyl" should read --1.75% t-amyl--.

Signed and Sealed this

Fifteenth Day of February 1983

[SEAL]

Attest:

GERALD J. MOSSINGHOFF

Attesting Officer     Commissioner of Patents and Trademarks